US012679910B2

(12) United States Patent
Wang et al.

(10) Patent No.: US 12,679,910 B2
(45) Date of Patent: Jul. 14, 2026

(54) POLY[ALPHA-CYANOACRYLATE] HYDROLYZATE AND PREPARATION METHOD AND APPLICATION THEREOF

(71) Applicant: DALIAN HEYUAN MEDICAL EQUIPMENTS CO., LTD., Dalian (CN)

(72) Inventors: Junping Wang, Dalian (CN); Yin Guo, Dalian (CN)

(73) Assignee: DALIAN HEYUAN MEDICAL EQUIPMENTS CO., LTD., Dalian (CN)

( * ) Notice: Subject to any disclaimer, the term of this patent is extended or adjusted under 35 U.S.C. 154(b) by 781 days.

(21) Appl. No.: 17/640,480

(22) PCT Filed: Aug. 21, 2020

(86) PCT No.: PCT/CN2020/110386
§ 371 (c)(1),
(2) Date: Mar. 4, 2022

(87) PCT Pub. No.: WO2021/043004
PCT Pub. Date: Mar. 11, 2021

(65) Prior Publication Data
US 2022/0332862 A1      Oct. 20, 2022

(30) Foreign Application Priority Data

Sep. 5, 2019    (CN) .......................... 201910836242.7
Sep. 5, 2019    (CN) .......................... 201910836249.9

(51) Int. Cl.
*C08F 120/50* (2006.01)
*A61K 9/50* (2006.01)
*C08F 8/12* (2006.01)
*C08F 122/00* (2006.01)

(52) U.S. Cl.
CPC .......... *C08F 120/50* (2013.01); *A61K 9/5026* (2013.01); *C08F 8/12* (2013.01); *C08F 122/00* (2013.01)

(58) Field of Classification Search
None
See application file for complete search history.

(56) References Cited

U.S. PATENT DOCUMENTS 4,013,703 A * 3/1977 Buck ..................... C07F 7/0838
558/429
2003/0157023 A1* 8/2003 Roessling ............ A61K 49/223
424/9.52

FOREIGN PATENT DOCUMENTS

CN         1424919 A  *  6/2003   ........... A61K 49/223
CN     110498877 A      11/2019
CN     110527007 A      12/2019

OTHER PUBLICATIONS

Birkinshaw et al.; "Hydrolysis of poly (n-butylcyanoacrylate) nanoparticles using esterase," 2002, Elsevier; Polymer Degradation and Stability, vol. 78, pp. 7-15. (Year: 2002).*
Rustamov et al.; "Polycyanoacrylate porous material for bone tissue substitution," 2014, RSC; Journal of Materials Chemistry B, vol. 2, pp. 4310-4317. (Year: 2014).*
Bootz et al.; "Molecular weights of poly(butyl cyanoacrylate) nanoparticles determined by mass spectrometry and size exclusion chromatography," 2005; Elsevier; European Journal of Pharmaceutics and Biopharmaceutics, vol. 60, pp. 391-399. (Year: 2005).*
International Search Report issued in corresponding International Application No. PCT/CN2020/110386, mailed Nov. 25, 2020; 3 pgs.
Written Opinion issued in corresponding International Application No. PCT/CN2020/110386, mailed Nov. 25, 2020; 6 pgs.

* cited by examiner

*Primary Examiner* — Tigabu Kassa
*Assistant Examiner* — Ivan A Greene
(74) *Attorney, Agent, or Firm* — HAUPTMAN HAM LLP

(57) ABSTRACT
The invention relates to a poly[α-cyanoacrylate] hydrolyzate, a preparation method and an application thereof, belonging to the field of pharmaceutical and chemical industry. A main technical solution is as follows: provided is a poly[α-cyanoacrylate] hydrolyzate having a chemical formula: $-[CH_2-CRCOOH]-_n$, wherein R=—CN or —COOH. Poly[2-cyanoacrylic acid] provided by the present invention is dispersed in water to prepare the negatively charged microsphere, that is, to obtain the new blank embolic microsphere, the particle size of the microsphere can be adjusted in a micron-scale range, and the microsphere have a deformation function to pass through a vascular with a specific shape, which can tightly embolize the vascular to avoid ectopic embolism caused by falling off; poly[2-carboxyacrylic acid] can be used for preparing a new nano-drug carrier, improving the curative effect of the carried drug on diseased tissues and reduce the toxic and side effects of the carried drug on normal tissues.

1 Claim, 4 Drawing Sheets

-[CH$_2$-C(COOH)$_2$]n- +NH$_2$-PEG2000 $\xrightarrow[\text{NHS}]{\text{EDC.HCl}}$ -[CH$_2$-C]$_n$-

PEG2000

COOH

POLY[ALPHA-CYANOACRYLATE] HYDROLYZATE AND PREPARATION METHOD AND APPLICATION THEREOF

RELATED APPLICATIONS

The present application is a U.S. National Phase of International Application Number PCT/CN2020/110386 filed Aug. 21, 2020, and claims priority to Chinese Application Numbers 2019108362499 filed Sep. 5, 2019, and 2019108362427, filed Sep. 5, 2019.

TECHNICAL FIELD

The invention relates to the field of pharmaceutical and chemical industry, in particular to a poly[α-cyanoacrylate] hydrolyzate, a preparation method and an application thereof.

BACKGROUND

It is generally believed that endovascular embolization should be avoided, but some vascular can receive good therapeutic results if they can be selectively partially embolized. In recent years, due to the development of medical technology, people have been able to inject a vascular occlusive agent into relevant arteries through inserted catheters to treat some diseases, especially for diseases that are difficult to control with surgery or drugs, such as tumors or gastric varices. This technique is medically known as selective vascular embolization. Transcatheter arterial embolization was first used in the 1970s to treat prostatic hemorrhage and intractable hematuria of prostatic origin after prostate biopsy or transurethral prostatic resection. During vascular embolization, embolic agents must be used. In addition to using some natural embolic substances such as blood clots, mechanical blockage can be performed with balloons, metal balls, spring tubes, etc. The embolic agents currently used are divided into two categories: solid embolic agents and liquid embolic agents, and some natural embolic agents are also comprised in the solid embolic agents.

There are many types of nano-drug carriers, among which liposomes have attracted much attention. Liposomes are mainly composed of cholesterol and phospholipids, which are similar in structure to cells, and can be used to carry drugs. There are two main problems with liposomes: firstly, how to load drugs, secondly, how to prevent liposomes from being phagocytosed and destroyed by a reticuloendothelial system and how to release drugs in diseased tissue. Liposomes have low toxicity, no immunogenicity, and no pyrogenicity, and can be eliminated through normal metabolism, so that the liposomes are ideal drug carriers. The current nanoliposome drugs are mainly prepared by actively loading drugs with the aid of ammonium ion gradient, such as Doxil, which is a liquid nano-doxorubicin liposome. However, a preparation process of this nanoliposome doxorubicin is complex, the stability is poor, and it is difficult for the nanoliposome doxorubicin to actively release drugs in tumor tissue.

SUMMARY

In view of the problems existing in the prior art, the present invention provides a poly[α-cyanoacrylate] hydrolyzate, a preparation method and an application thereof. The technical solution of the present invention is as follows:

provided is a poly[α-cyanoacrylate] hydrolyzate having a chemical formula:

$$-\!\!\left[CH_2-CRCOOH\right]_{\overline{n}}-,$$

wherein R=—CN or —COOH.

The invention also seeks to protect a preparation method for the poly[α-cyanoacrylate] hydrolyzate comprising firstly preparing an α-cyanoacrylate polymer, and hydrolyzing the polymer to obtain the poly[α-cyanoacrylate] hydrolyzate.

When R is —CN, the poly[α-cyanoacrylate] hydrolyzate is poly[2-cyanoacrylic acid], having a chemical formula:

$$-\!\!\left[CH_2-C\,(CN)\,(COOH)\right]_{\overline{n}}-.$$

A preparation method for the poly[2-cyanoacrylic acid] comprise firstly preparing an α-cyanoacrylate polymer, then selectively hydrolyzing the ester bond in the polymer under alkaline conditions, and performing purification to obtain the poly[2-cyanoacrylic acid].

The invention seeks to protect application of the poly[α-cyanoacrylate] hydrolyzate, wherein poly[2-cyanoacrylic acid] is prepared as the blank embolic microsphere.

Further, a preparation method for the blank embolic microsphere comprises dispersing poly[2-cyanoacrylic acid] in water to form negatively charged microsphere, that is, to obtain the blank embolic microsphere.

Further, a particle size of the blank embolic microsphere ≥1 μm, and the blank embolic microsphere can be deformed.

Further, the particle size of the blank embolic microsphere can be adjusted in a micron-scale range to accommodate the requirements of embolism targets of a vascular with different diameters, and meanwhile, the blank embolic microsphere have a deformation function as required to pass through vascular stenosis in an embolic pathway, which can closely embolize the vascular to avoid ectopic embolism caused by falling off.

In the present invention, poly[2-cyanoacrylic acid] is prepared as the blank embolic microsphere, and the blank embolic microsphere are prepared as the drug-loaded embolic microsphere.

Further, a preparation method for the drug-loaded embolic microsphere comprises combining the blank embolic microsphere with a positively charged drug to obtain the drug-loaded embolic microsphere.

Further, the drug-loaded embolic microsphere actively load (pH≥7.4) and release (pH≤6.5) drugs based on a charge reversal principle.

Further, the drug-loaded embolic microsphere can directly release drugs into a local area of the diseased tissue in diseased tissue with high vascular permeability and a low pH value, and the drugs rarely flow throughout the whole body, thereby improving the local efficacy of the drugs on the diseased tissue and reducing the toxic and side effects of the drugs on the whole body.

More particularly preferred preparation methods and applications are as follows:

1. Preparation of poly[2-cyanoacrylic acid]

(1) Method 1:

An emulsion of α-cyanoacrylate or its vegetable oil solution is prepared with a nonionic surfactant such as a polyethylene glycol nonionic surfactant or a Tween surfactant or an Span surfactant or poloxamer in physiological saline or a 5% or above dextrose solution or a 5% or above dextran solution with a pH value of 2.0-4.0. Then the pH value is adjusted to 7.4 or above, and an accelerated polymerization reaction is carried out to form an α-cyanoacrylate polymer. Then ester bonds of the polymer are hydrolyzed selectively under alkaline conditions and cyano group is retained, vegetable oil will be saponified, and impurities are removed by dialysis to obtain poly[2-cyanoacrylic acid].

The higher the content of the nonionic surfactant, the less the usage amount of α-cyanoacrylate, the smaller the particle size of the emulsion. A polymerization degree of poly[2-cyanoacrylic acid] can be controlled by the particle size of the α-cyanoacrylate emulsion. The smaller the particle size of the emulsion, the smaller the polymerization degree.

Poly[2-cyanoacrylic acid] of different molecular weights can be prepared through dialysis or separation by gel chromatography.

(2) Method 2:

α-cyanoacrylate is dissolved in anhydrous ethanol or acetone or acetonitrile. Under the condition of high-speed dispersion in a hard plastic disperser, the solution of the α-cyanoacrylate in the anhydrous ethanol or acetonitrile or acetone is slowly added dropwise into acidic water to be magnetically stirred overnight. High-speed centrifugation is performed to collect the obtained α-cyanoacrylate polymerization precipitate. Then ester bonds of the polymer are hydrolyzed selectively under alkaline conditions and cyano group is retained, and impurities are removed by dialysis to obtain poly[2-cyanoacrylic acid].

A polymerization degree of poly[2-cyanoacrylic acid] can be determined by the concentration of the α-cyanoacrylate, and the lower the concentration, the lower the polymerization degree.

Poly[2-cyanoacrylic acid] of different molecular weights can be prepared through dialysis or separation by gel chromatography.

2. Preparation of poly[2-cyanoacrylic acid] Blank Embolic Microsphere

By controlling the polymerization time of poly[α-cyanoacrylate] or the concentration of α-cyanoacrylate, the degree of polymerization is controlled, so that the particle size of the blank embolic microsphere can be controlled.

Poly[2-cyanoacrylic acid] is rich in carboxy. Under alkaline conditions, the carboxy group of the blank embolic microsphere have negative charges, and a repulsive force is generated between the negative charges. Therefore, the blank embolic microsphere have elasticity and deformation capacity.

(1) Method 1:

Poly[2-cyanoacrylic acid] has a certain surface activity and is easily soluble in anhydrous ethanol. An ethanol solution of poly[2-cyanoacrylic acid] is dispersed in water to prepare blank embolic microsphere rich in carboxy.

(2) Method 2:

Poly[2-cyanoacrylic acid] has a certain surface activity and is easily soluble in anhydrous ethanol. An ethanol solution of poly[2-cyanoacrylic acid] is dispersed in water, and partial carboxy group of poly[2-cyanoacrylic acid] are modified with active polyethylene glycol to obtain the blank embolic microsphere with modified carboxy.

Polyethylene glycol combined with polymer carboxy can effectively prevent a reticuloendothelial system from rapid phagocytosis and destruction of poly[2-cyanoacrylic acid], a framework material of the blank embolic microsphere, and unmodified carboxy is used to actively load positively charged drugs.

An optimal ratio of carboxy modification is related to the amount of a drug carried and the type of a drug, when the molecular weight of the drug is relatively large, and the hydrophilicity is poor, a proportion of modified carboxy should be higher, and when the molecular weight of the drug is relatively small, and the hydrophilicity is strong, a proportion of the modified carboxy can be lower. In addition, the proportion of the modified carboxy is also related to individual differences in application. It is necessary to ensure that the reticuloendothelial system cannot quickly destroy the blank embolic microsphere. In short, the specific carboxy modification ratio and the molecular weight of active polyethylene glycol should be specifically formulated according to clinical needs.

3. Application of poly[2-cyanoacrylic acid] Blank Embolic Microsphere

The particle size of the poly[2-cyanoacrylic acid] blank embolic microsphere can be adjusted according to clinical needs, and the blank embolic microsphere have elasticity and deformation capacity. When the particle size is greater than or equal to 8 μm, embolization treatment is performed to pass through specific vascular stenosis, and the microsphere are difficult to fall off due to close interaction with a vascular wall, and thus, ectopic embolism does not be produced.

4. Preparation of poly[2-cyanoacrylic acid] Drug-Loaded Embolic Microsphere

The poly[2-cyanoacrylic acid] blank embolic microsphere are combined with various positively charged drugs to obtain various drug-loaded embolic microsphere.

5. Application of poly[2-cyanoacrylic acid] Drug-Loaded Embolic Microsphere

According to clinical needs, the drug-loaded embolic microsphere can be loaded with different one or more positively charged drugs, local embolization therapy with specific requirements is performed, the drug-loaded embolic microsphere can directly release drugs into a local area of the diseased tissue in diseased tissue with high vascular permeability and a low pH value, and the drugs rarely flow throughout the whole body, thereby improving the local efficacy of drugs on the diseased tissue and reducing the toxic and side effects of drugs on the whole body.

When R is —COOH, the poly[α-cyanoacrylate] hydrolyzate is poly[2-carboxyacrylic acid] having a chemical formula:

$$-\!\!\left[CH_2\!-\!C\,(COOH)_2\right]_{\overline{n}}\!-\!\cdot$$

A preparation method for the poly[2-carboxyacrylic acid] comprises firstly preparing an α-cyanoacrylate polymer, then hydrolyzing the ester bond and the cyano group of the polymer under alkaline conditions, and dialyzing to remove impurities to obtain the poly[2-carboxyacrylic acid].

The invention seeks to protect application of the poly[α-cyanoacrylate] hydrolyzate, wherein poly[2-carboxyacrylic acid] is prepared as a nano-drug carrier.

Further, a preparation method for the nano-drug carrier comprises modifying partial carboxy of poly[2-carboxyacrylic acid] with active polyethylene glycol, and using unmodified carboxy to carry positively charged drugs to obtain a new nano-drug carrier with the function of actively loading (pH≥7.4) and releasing (pH≤6.5) positively charged drugs by means of a pH gradient.

Further, a preparation method for the nano-drug carrier comprises encapsulating poly[2-carboxyacrylic acid] in a liposome to obtain a new nanoliposome with the function of actively loading (pH≥7.4) and releasing (pH≤6.5) positively charged drugs by means of a pH gradient, wherein the new nanoliposome is also a nano-drug carrier.

Further, the nano-drug carrier actively loads and releases drugs based on a charge reversal principle.

Further, the nano-drug carrier targetedly delivers drugs through blood, the nano-drug carrier accumulates into diseased tissue with high vascular permeability and a low pH value, and directly releases drugs into the diseased tissue, and the drugs rarely enter normal tissues, and the carried drugs have enhanced efficacy on the diseased tissue and reduce the toxic and side effects on the normal tissue.

More particularly preferred preparation methods and applications are as follows:

1. Preparation of poly[2-carboxyacrylic acid]

(3) Method 1:

An emulsion of α-cyanoacrylate or its vegetable oil solution is prepared with a nonionic surfactant such as a polyethylene glycol nonionic surfactant or a Tween surfactant or a Span surfactant or poloxamer in physiological saline or a 5% or above dextrose solution or a 5% or above dextran solution with a pH value of 2.0-4.0. Then the pH value is adjusted to 7.4 or above, and an accelerated polymerization reaction is carried out to form an α-cyanoacrylate polymer. Then the ester bond and the cyano group of the polymer are hydrolyzed under alkaline conditions, vegetable oil will be saponified, and impurities are removed by dialysis to obtain poly[2-carboxyacrylic acid].

The higher the content of the nonionic surfactant, the less the usage amount of α-cyanoacrylate, the smaller the volume of a microemulsion. A polymerization degree of poly[2-carboxyacrylic acid] can be controlled by the size of the α-cyanoacrylate microemulsion. The smaller the microemulsion, the smaller the polymerization degree.

Poly[2-carboxyacrylic acid] of different molecular weights can be prepared through dialysis or separation by gel chromatography.

(4) Method 2:

α-cyanoacrylate is dissolved in anhydrous ethanol or acetone or acetonitrile. Under the condition of high-speed dispersion in a hard plastic disperser, the solution of the α-cyanoacrylate in the anhydrous ethanol or acetonitrile or acetone is slowly added dropwise into acidic water to be magnetically stirred overnight. High-speed centrifugation is performed to collect the obtained α-cyanoacrylate polymerization precipitate. Then ester bond and the cyano group of the polymer are hydrolyzed under alkaline conditions, and impurities are removed by dialysis to obtain poly[2-carboxyacrylic acid].

A polymerization degree of poly[2-carboxyacrylic acid] can be determined by the concentration of the α-cyanoacrylate, and the lower the concentration, the lower the polymerization degree.

Poly[2-carboxyacrylic acid] of different molecular weights can be prepared through dialysis or separation by gel chromatography.

2. Preparation of poly[2-carboxyacrylic acid] Nano-Drug Carrier (1) Method 1:

A poly[2-carboxyacrylic acid] nano-drug carrier is obtained by modifying partial carboxy of poly[2-carboxyacrylic acid] with active polyethylene glycol.

Polyethylene glycol combined with polymer carboxy can effectively prevent a reticuloendothelial system from rapid phagocytosis and destruction of poly[2-carboxyacrylic acid], a framework material of the nano-drug carrier, and unmodified carboxy is used to actively load positively charged drugs.

An optimal ratio of carboxy modification is related to the amount of a drug carried and the type of a drug, when the molecular weight of the drug is relatively large, and the hydrophilicity is poor, a proportion of modified carboxy should be higher, and when the molecular weight of the drug is relatively small, and the hydrophilicity is strong, a proportion of the modified carboxy can be lower. In addition, the proportion of the modified carboxy is also related to individual differences in application. It is necessary to ensure that the reticuloendothelial system cannot quickly destroy the nano-drug carrier. In short, the specific carboxy modification ratio and the molecular weight of active polyethylene glycol should be specifically formulated according to clinical needs.

(2) Method 2:

Phospholipid, cholesterol, PEG2000-DSPE and poly[2-carboxyacrylic acid] are dissolved in anhydrous ethanol, a liposome encapsulating poly[2-carboxyacrylic acid] inside is prepared by a thin film method, gel chromatography is used to remove poly[2-carboxyacrylic acid] outside the liposome to obtain a nanoliposome encapsulating poly[2-carboxyacrylic acid], and then, a pH value of an aqueous phase outside the nanoliposome is adjusted to 7.4, so that a pH gradient inside and outside the liposome is 5.0 or above to obtain a nanoliposome with the function of actively loading positively charged drugs, wherein the nanoliposome is also a nano-drug carrier.

According to the Henderson-Hasselbalch theory, each pH unit change will produce a 10-fold difference between molecular and ionic drug concentrations. If the pH gradient inside and outside the liposome is 3.0, a 1000-fold difference between molecular and ionic drug concentrations will be theoretically caused. Because molecular drugs are likely to bind to a liposome bimolecular membrane, a transmembrane aversion process of drug molecules is accelerated.

Poly[2-carboxyacrylic acid] is combined with positively charged drugs to form a precipitate, which will further promote the entry of the positively charged drugs into the nanoliposome and improve the drug delivery ability of the nanoliposome.

3. Application of poly[2-carboxyacrylic acid] Nano-Drug Carrier

The nano-drug carrier prepared by using poly[2-carboxyacrylic acid] can actively load positively charged drugs with the help of carboxy under alkaline conditions such as pH=7.4, and vice versa, under acidic conditions such as pH=6.5, the carried positively charged drugs will be released spontaneously.

Normal tissues have low vascular permeability and a high pH value (close to 7.4), while diseased tissues have high vascular permeability and a low pH value (close to 6.5). Therefore, after entering a blood circulation system, the nano-drug carrier will gradually accumulate into the diseased tissues and release the drugs carried, thereby improving the curative effect of the drugs on the diseased tissues (except for a prodrug) and reducing the toxic and side effects of the drugs on the normal tissues.

The benefit effects of the present invention are as follows:

(1) a preparation method for a new material carboxy-rich poly[2-cyanoacrylic acid] is provided;

(2) poly[2-cyanoacrylic acid] can be used for preparing new blank embolic microsphere;

(3) the new blank embolic microsphere have adjustable particle size and deformation capacity to pass through stenosis;

(4) the new blank embolic microsphere can be used to prepare new drug-loaded embolic microsphere;

(5) the new drug-loaded embolic microsphere can improve the local efficacy of the carried drugs on the diseased tissues;

(6) the new drug-loaded embolic microsphere can reduce the toxic and side effects of the carried drugs on the whole body;

(7) in the foreign DC-bead prior art (as shown in FIG. 1), N-acryloyl-aminoacetaldehyde-dimethyl acetal, and butyl acetate must be used, which has high volatility and large residue, which is not conducive to the production environment and has low safety. In the present invention, α-cyanoacrylate, vegetable oil, dextrose, physiological saline, the nonionic surfactant, active polyethylene glycol, anhydrous ethanol, pure water, etc., are only used, without toxic residue and pollution, the process is simple, the production cost is low and the safety is high;

(8) the number of molecules loaded with anticancer drugs per unit volume in the foreign DC-bead is relatively small. According to the calculation of the chemical structure, about 50% of carbon atoms in the molecular structure of the drug-loaded embolic microsphere prepared by the present invention carry one carboxy negative charge, while about 20% of carbon atoms in the DC-bead molecule carry one carboxy negative charge. The total amount of negative charges per unit mass of the drug-loaded embolic microsphere prepared by the present invention is significantly higher than that of the DC-bead, and the ability to load drugs is significantly improved;

(9) the foreign DC-bead is a sulfonic acid group with strong acidity, and its ability to selectively release drugs in the vicinity of tumor tissues is weak. The carboxy carried by the drug-loaded embolic microsphere prepared by the present invention is less acidic, and the release rate of the drug is different under different pH conditions, and the release rate of the drugs is significantly accelerated near the tumor tissue with a low pH value, and thus, the drug-loaded embolic microsphere have the characteristics of strong selective release of the drugs near the tumors;

(10) a preparation method for a new material carboxy-rich poly[2-carboxyacrylic acid] is provided;

(11) poly[2-carboxyacrylic acid] can be used to prepare a new nano-drug carrier;

(12) the new nano-drug carrier can improve the curative effect of the carried drugs on diseased tissues; and

(13) the new nano-drug carrier can reduce the toxic and side effects of the carried drugs on normal tissues.

DETAILED DESCRIPTION

Figures 1, 2:
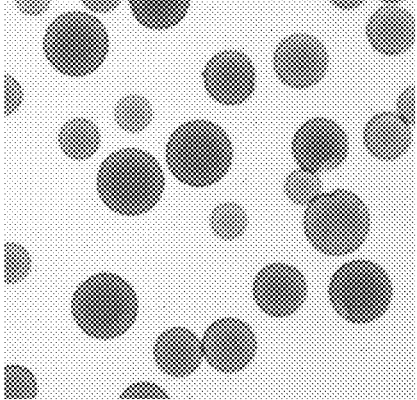
FIG. 1 is a diagram showing a traditional DC-Bead preparation process.
FIG. 2 shows the blank embolic microsphere (50×)

The present invention will be further illustrated and explained below with reference to specific examples, and unless otherwise specified, raw materials and equipment used in the present invention are common raw materials and equipment.

Example 1 Preparation of poly[2-cyanoacrylic acid]

(1) Formula: n-butyl α-cyanoacrylate

Physiological Saline, Sesame Oil, Tween-80, Span-20, and Anhydrous Ethanol n-butyl α-cyanoacrylate was dissolved in refined sesame oil without pyrogen to form 10 mL of a 30% oil solution of n-butyl α-cyanoacrylate, and the oil solution of n-butyl α-cyanoacrylate was dispersed in a 0.25% physiological saline solution of Tween-80 and span-20 with a pH value of 4.0. The pH value was adjusted to 7.8, a polymerization reaction of n-butyl α-cyanoacrylate was initiated, centrifugation was performed to separate a precipitate after 12 hours, the precipitate was washed with anhydrous ethanol, and centrifugation was repeatedly performed for 5 times. The precipitate was dispersed in 50 ml of anhydrous ethanol, and sodium hydroxide was added to selectively hydrolyze the ester bond and retain the cyano group. The anhydrous ethanol was removed by evaporation under reduced pressure, then the resulting residue was mixed with 100 mL of distilled water, the mixture was centrifuged at 8000 rpm for 20 min, the supernatant was discarded, water washing was performed while shaking, centrifugation was performed again, and the operations were repeatedly performed for 5 times to obtain poly[2-cyanoacrylic acid].

(2) Formula: octyl α-cyanoacrylate

A 50% Dextrose Solution, Poloxamer, and Anhydrous Ethanol

Octyl α-cyanoacrylate was dissolved in a 50% dextrose solution of 0.25% poloxamer with a pH value of 4.0 to form an octyl α-cyanoacrylate emulsion, the pH value was adjusted to 7.4, polymerization was carried out at room temperature for 12 hours under stirring, centrifugation was performed to separate a precipitate, the precipitate was dispersed in 50 ml of anhydrous ethanol, sodium hydroxide was added to selectively hydrolyze ester bonds and retain cyano, the anhydrous ethanol was removed by evaporation under reduced pressure, then the resulting residue was mixed with 100 mL of distilled water, the mixture was centrifuged at 8000 rpm for 20 min, the supernatant was discarded, water washing was performed while shaking, centrifugation was performed again, and the operations were repeatedly performed for 5 times to obtain poly[2-cyano-acrylic acid].

(3) Formula: isobutyl α-cyanoacrylate

A 10% Dextran Solution, Polyethylene Glycol 400 Monooleate, and Anhydrous Ethanol Isobutyl α-cyanoacrylate was dissolved in a 10% dextran solution of 0.25% polyethylene glycol 400 monooleate with a pH value of 4.0 to form an isobutyl α-cyanoacrylate emulsion, the pH value was adjusted to 7.4, polymerization was carried out at room temperature for 12 hours under stirring, centrifugation was performed to separate a precipitate, then the precipitate was dispersed in 50 ml of anhydrous ethanol, sodium hydroxide was added to selectively hydrolyze ester bonds and retain cyano, the anhydrous ethanol was removed by evaporation under reduced pressure, then the resulting residue was mixed with 100 mL of distilled water, the mixture was centrifuged at 8000 rpm for 20 min, the supernatant was discarded, water washing was performed while shaking, centrifugation was performed again, and the operations were repeatedly performed for 5 times to obtain poly[2-cyanoacrylic acid].

(4) Formula: n-butyl α-cyanoacrylate

Anhydrous Ethanol n-butyl α-cyanoacrylate was dissolved in anhydrous ethanol to make a 50% ethanol solution, polymerization was carried out for 1 week, then sodium hydroxide was added to selectively hydrolyze ester bonds and retain cyano, the anhydrous ethanol was removed by evaporation under reduced pressure, then the resulting residue was mixed with 100 mL of distilled water, the mixture was centrifuged at 8000 rpm for 20 min, the supernatant was discarded, water washing was performed while shaking, centrifugation was performed again, and the operations were repeatedly performed for 5 times to obtain poly[2-cyanoacrylic acid].

(5) Formula: methyl α-cyanoacrylate

Acetone, and Anhydrous Ethanol

Methyl α-cyanoacrylate was dissolved in acetone to make a 50% acetone solution, polymerization was carried out for 2 weeks, acetone was removed under reduced pressure, the resulting residue was dispersed in anhydrous ethanol, then sodium hydroxide was added to selectively hydrolyze ester bonds and retain cyano, the anhydrous ethanol was removed by evaporation under reduced pressure, the resulting residue was mixed with 100 mL of distilled water, the mixture was centrifuged at 8000 rpm for 20 min, the supernatant was discarded, water washing was performed while shaking, centrifugation was performed again, and the operations were repeatedly performed for 5 times to obtain poly[2-cyano-acrylic acid].

(6) Formula: ethyl α-cyanoacrylate

Acetonitrile, and Anhydrous Ethanol

Ethyl α-cyanoacrylate was dissolved in acetonitrile to make a 50% acetonitrile solution, polymerization was carried out for 2 weeks, then the acetonitrile was removed under reduced pressure, the resulting residue was dispersed in anhydrous ethanol, then sodium hydroxide was added to selectively hydrolyze ester bonds and retain cyano, the anhydrous ethanol was removed by evaporation under reduced pressure, the resulting residue was mixed with 100 mL of distilled water, the mixture was centrifuged at 8000 rpm for 20 min, the supernatant was discarded, water washing was performed while shaking, centrifugation was performed again, and the operations were repeatedly performed for 5 times to obtain poly[2-cyanoacrylic acid].

Example 2 Preparation of poly[2-cyanoacrylic acid] Blank Embolic Microsphere (1) Formula: poly[2-cyanoacrylic acid]

Anhydrous Ethanol, and Water 0.5 g of poly[2-cyanoacrylic acid] was prepared into 5 mL of an anhydrous ethanol solution. The solution was placed in a rotary evaporator, the ethanol was evaporated to form a film on a wall of the rotary evaporator, mixed with 50 mL of distilled water, hydration was performed for 12 h, centrifugation was performed at 8000 rpm for 20 min, the supernatant was discarded, water washing was performed while shaking, centrifugation was performed again, and the operations were repeatedly performed for 5 times to obtain the blank embolic microsphere.

(2) Formula: poly[2-cyanoacrylic acid]

Amino Polyethylene Glycol 2000, and Water carboxy was modified with amino polyethylene glycol 2000, an active polyethylene glycol modified catalyst:
EDC·HCl: 1-(3-dimethylaminopropyl)-3-ethylcarbodiimide hydrochloride;
NETS: N-hydroxysuccinimide. After polyethylene glycol modification, centrifugation was performed at 8000 rpm for 20 min, the supernatant was discarded, water washing was performed while shaking, centrifugation was performed again, and the operations were repeatedly performed for 5 times to obtain polyethylene glycol modified blank embolic microsphere.

Example 3 Preparation of poly[2-cyanoacrylic acid] Drug-Loaded Embolic Microsphere (1) Formula: The Blank Embolic Microsphere Doxorubicin 1 mL of the blank embolic microsphere was mixed with an equal volume of 2 mg/mL doxorubicin 1/15 M isotonic phosphate buffer with a pH value of 7.4, the mixture was shaked for 15 min, the remaining doxorubicin solution was poured out, and then rinsing was performed with 1/15 M isotonic phosphate buffer with a pH value of 7.4 to obtain the doxorubicin-loaded embolic microsphere for tumor arterial embolization.

(2) Formula: The Blank Embolic Microsphere

Gentamicin 1 mL of the blank embolic microsphere was mixed with an equal volume of 10 mg/mL gentamicin 1/15 M isotonic phosphate buffer solution with a pH value of 7.4, the mixture was shaked for 5 min, the remaining gentamicin solution was poured out, and then rinsing was performed with 1/15 M isotonic phosphate buffer solution with a pH value of 7.4 to obtain gentamicin-loaded embolic microsphere with anti-inflammatory treatment requirements.

Efficacy of poly[2-cyanoacrylic] embolic Microsphere

1. New Blank Embolic Microsphere

The particle size and surface morphology of the new blank embolic microsphere were observed and measured by optical microscope and scanning electron microscope (as shown in FIG. 2). The particle size changes of the new blank embolic microsphere during long-term storage were measured at different storage temperatures. The new blank embolic microsphere can be used for embolization treatment of arterial bleeding, such as traumatic pelvic and visceral bleeding, urinary system bleeding, gastrointestinal bleeding, severe nasal and maxillofacial bleeding, massive hemoptysis, and postoperative visceral bleeding, and can also be used for embolization treatment of venous bleeding, such as gastrointestinal varices.

2. New Drug-Loaded Embolic Microsphere

Figure 3:
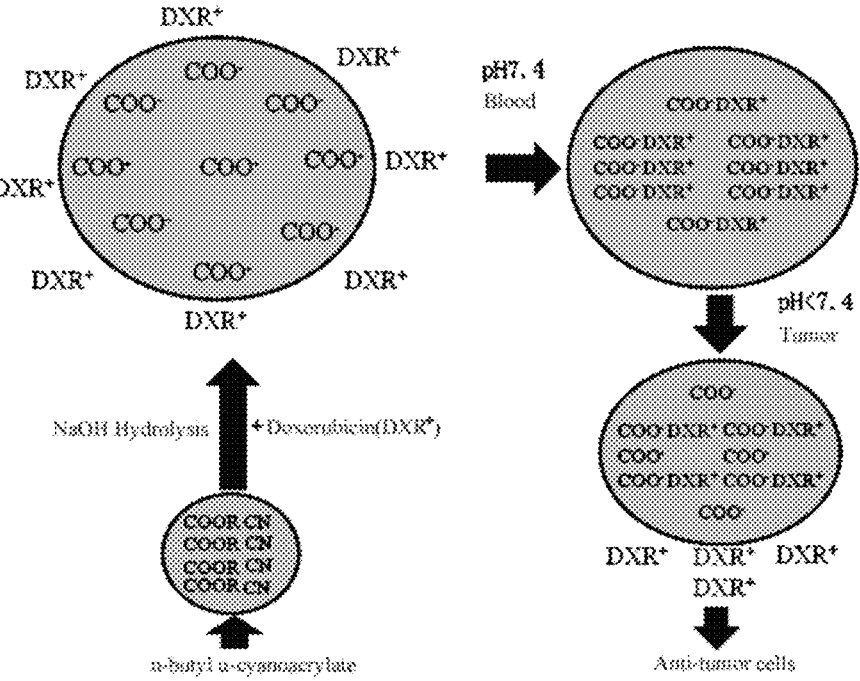
FIG. 3 is a diagram showing preparation and functioning of the drug-loaded embolic microsphere.
Figure 4:
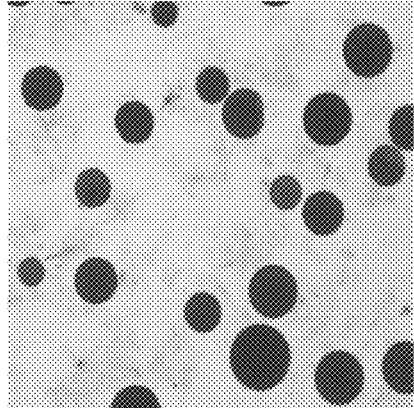
FIG. 4 shows the doxorubicin-loaded embolic microsphere (50×)
Figure 5:
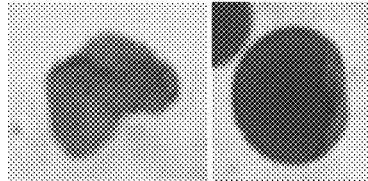
FIG. 5 shows an internal morphology of the doxorubicin-loaded embolic microsphere after pulverization.

The drug loading rate, drug automatic loading rate and drug release rate of the new drug-loaded embolic microsphere were determined by a UV-Vis spectrophotometer. A rabbit model of VX2 liver cancer was established by a tumor tissue block embedding method, and the effectiveness of doxorubicin-loaded embolic microsphere in the hepatic artery was evaluated (as shown in FIG. 3). Two weeks after the embedding implantation of a tumor mass, the doxorubicin-loaded embolic microsphere were injected by open hepatic artery intubation (as shown in FIG. 4). The concentration of doxorubicin in peripheral blood of experimental rabbits was determined by high performance liquid chromatography (HPLC). The doxorubicin distribution in the tumor mass and the tumor microvessel density were observed by an immunofluorescence staining technology. The results showed that the size of the new drug-loaded embolic microsphere could effectively embolize tumor arterial vascular, and the anti-tumor effect was remarkable, and the tumor vessel density was significantly reduced. Animal experiments have shown that this new drug-loaded embolic microspheres can also be used for the treatment of renal cancer, adrenal cancer, various vascular-rich tumors in the pelvis, maxillofacial malignant tumors, and limbic, spinal and pelvic malignant tumors. The new drug-loaded embolic microsphere can also be loaded with all positively charged drugs, can be used for vascular embolization treatment with specific needs, can improve the local efficacy of drugs on diseased tissues and reduce the toxic and side effects of drugs on the whole body (as shown in FIG. 5).

Example 4 Preparation of poly[2-carboxyacrylic acid]

| (1) Formula: n-butyl α-cyanoacrylate | 0.9 mL |
|---|---|
| Tween-80 | 3.0 mL |
| physiological saline (pH 2.0) | 50 mL |

Preparation process: Tween-80 was dissolved in physiological saline, a pH value was adjusted to 2.0 with 0.01N hydrochloric acid, n-butyl α-cyanoacrylate was slowly added dropwise under the condition of high-speed dispersion with a rigid plastic rotor within 9 min, the mixture was dispersed at high speed in ice water for 45 min with a hard plastic tissue disperser, filtering was performed with a 0.45 μm microporous filter membrane, the pH value was adjusted to 7.8 with 0.01N sodium hydroxide, the resulting solution was stored overnight, centrifuged at low temperature at 8000 rpm for 20 min, and washed with 50% ethanol for 3 times, a precipitate being retained during centrifuging at 8000 rpm for 20 min each time, 95% ethanol was added, hydrolysis was performed with 0.1N sodium hydroxide to obtain a light yellow solution, rotary evaporation was performed to remove the solvent, the pH value was adjusted to 7.4 with 0.1N hydrochloric acid, pure water dialysis was performed with a dialysis bag with a molecular weight lower limit of 10000, a dialysis solution being changed once every 12 hours, and freeze drying was performed to obtain poly[2-carboxyacrylic acid].

| (2) Formula: octyl α-cyanoacrylate | 0.9 mL |
|---|---|
| polyethylene glycol 400 monooleate | 6.0 mL |
| 50% dextrose (pH 2.0) | 50 mL |

Preparation process: polyethylene glycol 400 monooleate was added to 50% dextrose, a pH value was adjusted to 2.0 with 0.01N hydrochloric acid, octyl α-cyanoacrylate was slowly added dropwise under the condition of high-speed dispersion with a rigid plastic rotor within 9 min, the mixture was dispersed in ice water for 5 min with a hard plastic tissue disperser, filtering was performed with a 0.45 μm microporous filter membrane, the pH value was adjusted to 7.8 with 0.01N sodium hydroxide, the resulting solution was continued to be dispersed overnight, centrifuged at low temperature at 8000 rpm for 40 min, and washed for three times with pure water, a precipitate being retained during centrifuging at 8000 rpm for 20 min each time, an appropriate amount of 95% ethanol was added, hydrolysis was performed with 0.1N sodium hydroxide to obtain a light yellow solution, rotary evaporation was performed to remove the solvent, the pH value was adjusted to 7.4 with 0.1N hydrochloric acid, pure water dialysis was performed with a dialysis bag with a molecular weight lower limit of 10000, a dialysis solution being changed once every 12 hours, and freeze drying was performed to obtain poly[2-carboxyacrylic acid].

| (3) Formula: n-butyl α-cyanoacrylate | 0.9 mL |
|---|---|
| refined soybean oil | 2.1 mL |
| Tween-80 | 6.0 mL |
| Span-20 | 1.2 mL |
| 20% dextrose (pH 2.0) | 50 mL |

Preparation process: Tween-80 and Span-20 were added to 20% dextrose, a pH value was adjusted to 2.0 with 0.01N hydrochloric acid, n-butyl α-cyanoacrylate was added to soybean oil to prepare a solution with good flowability, the soybean oil solution of n-butyl α-cyanoacrylate was slowly added dropwise under the condition of high-speed dispersion with a rigid plastic rotor within 9 min, the mixture was dispersed in ice water for 5 min with a hard plastic tissue disperser, filtering was performed with a 0.45 μm microporous filter membrane, the pH value was adjusted to 12 with 0.01N sodium hydroxide, the resulting solution was continued to be dispersed overnight, centrifuged at low temperature at 8000 rpm for 40 min, and washed with pure water for 3 times, a precipitate being retained during centrifuging at 8000 rpm for 20 min each time, an appropriate amount of 95% ethanol was added, hydrolysis was performed with 0.1N sodium hydroxide to obtain a light yellow solution, rotary evaporation was performed to remove the solvent, the pH value was adjusted to 7.4 with 0.1N hydrochloric acid, pure water dialysis was performed with a dialysis bag with a molecular weight lower limit of 10000, a dialysis solution being changed once every 12 hours, and freeze drying was performed to obtain poly[2-carboxyacrylic acid].

| (4) Formula: isobutyl α-cyanoacrylate | 0.9 mL |
| poloxamer | 6.0 mL |
| 5% dextran (pH 2.0) | 50 mL |

Preparation process: poloxamer was added to 5% dextran, a pH value was adjusted to 2.0 with 0.01N hydrochloric acid, isobutyl α-cyanoacrylate was slowly added dropwise under the condition of high-speed dispersion with a rigid plastic rotor within 9 min, the mixture was dispersed in ice water for 5 min with a hard plastic tissue disperser, filtering was performed with a 0.45 μm microporous filter membrane, the pH value was adjusted to 7.8 with 0.01N sodium hydroxide, the resulting solution was continued to be dispersed overnight, centrifuged at low temperature at 8000 rpm for 40 min, and washed with pure water for 3 times, a precipitate being retained during centrifuging at 8000 rpm for 20 min each time, an appropriate amount of 95% ethanol was added, hydrolysis was performed with 0.1N sodium hydroxide to obtain a light yellow solution, rotary evaporation was performed to remove the solvent, the pH value was adjusted to 7.4 with 0.1N hydrochloric acid, pure water dialysis was performed with a dialysis bag with a molecular weight lower limit of 10000, a dialysis solution being changed once every 12 hours, and freeze drying was performed to obtain poly[2-carboxyacrylic acid].

| (5) Formula: n-butyl α-cyanoacrylate | 0.9 mL |
| anhydrous ethanol | 5.0 mL |
| water (pH 2.0) | 50 mL |

Preparation process: n-butyl α-cyanoacrylate was added to anhydrous ethanol to form a clear solution, the anhydrous ethanol solution of n-butyl α-cyanoacrylate was slowly added dropwise under the condition of high-speed dispersion with a rigid plastic rotor within 9 min, the solution was dispersed in ice water for 15 min with a hard plastic tissue disperser, filtering was performed with a 0.45 μm microporous filter membrane, the pH value was adjusted to 7.8 with 0.01N sodium hydroxide, the resulting solution was continued to be dispersed overnight, centrifuged at low temperature at 8000 rpm for 15 min, and washed with pure water for 3 times, a precipitate being retained during centrifuging at 8000 rpm for 15 min each time, an appropriate amount of 95% ethanol was added, hydrolysis was performed with 0.1N sodium hydroxide to obtain a light yellow solution, rotary evaporation was performed to remove the solvent, the pH value was adjusted to 7.4 with 0.1N hydrochloric acid, pure water dialysis was performed with a dialysis bag with a molecular weight lower limit of 10000, a dialysis solution being changed once every 12 hours, and freeze drying was performed to obtain poly[2-carboxyacrylic acid].

| (6) Formula: methyl α-cyanoacrylate | 0.9 mL |
| acetone | 5.0 mL |
| water (pH 2.0) | 50 mL |

Preparation process: methyl α-cyanoacrylate was added to acetone to form a clear solution, the acetone solution of methyl α-cyanoacrylate was slowly added dropwise under the condition of high-speed dispersion with a rigid plastic rotor within 9 min, the solution was dispersed in ice water for 15 min with a hard plastic tissue disperser, filtering was performed with a 0.45 μm microporous filter membrane, the pH value was adjusted to 7.8 with 0.01N sodium hydroxide, the resulting solution was continued to be dispersed overnight, centrifuged at low temperature at 8000 rpm for 15 min, and washed with pure water for 3 times, a precipitate being retained during centrifuging at 8000 rpm for 15 min each time, an appropriate amount of 95% ethanol was added, hydrolysis was performed with 0.1N sodium hydroxide to obtain a light yellow solution, rotary evaporation was performed to remove the solvent, the pH value was adjusted to 7.4 with 0.1N hydrochloric acid, pure water dialysis was performed with a dialysis bag with a molecular weight lower limit of 10000, a dialysis solution being changed once every 12 hours, and freeze drying was performed to obtain poly[2-carboxyacrylic acid].

| (7) Formula: ethyl α-cyanoacrylate | 0.9 mL |
| acetonitrile | 5.0 mL |
| water (pH 2.0) | 50 mL |

Preparation process: ethyl α-cyanoacrylate was added to acetonitrile to form a clear solution, the acetonitrile solution of ethyl α-cyanoacrylate was slowly added dropwise under the condition of high-speed dispersion with a rigid plastic rotor within 9 min, the solution was dispersed in ice water for 15 min with a hard plastic tissue disperser, filtering was performed with a 0.45 μm microporous filter membrane, the pH value was adjusted to 7.8 with 0.01N sodium hydroxide, the resulting solution was continued to be dispersed overnight, centrifuged at low temperature at 8000 rpm for 15 min, and washed with pure water for 3 times, a precipitate being retained during centrifuging at 8000 rpm for 15 min each time, an appropriate amount of 95% ethanol was added, hydrolysis was performed with 0.1N sodium hydroxide to obtain a light yellow solution, rotary evaporation was performed to remove the solvent, the pH value was adjusted to 7.4 with 0.1N hydrochloric acid, pure water dialysis was performed with a dialysis bag with a molecular weight lower limit of 10000, a dialysis solution being changed once every 12 hours, and freeze drying was performed to obtain poly[2-carboxyacrylic acid].

Example 5 Preparation of poly[2-carboxyacrylic acid] Nano-Drug Carrier

| (1) Formula: poly[2-carboxyacrylic acid] | 590 mg |
| aminopolyethylene glycol 2000 | 2000 mg |

Preparation process: under the condition of magnetic stirring, with 1-(3-dimethylaminopropyl)-3-ethylcarbodiimide hydrochloride (1-ethyl-3-(3-dimethylaminopropyl)carbodiimide, EDC·HCl), and N-hydroxy succinimide (NHS) as a catalyst, 2 g of NH₂-PEG was added to a nano-drug carrier framework solution to modify a nano-drug carrier framework, a reaction was carried out overnight, the above solution was put into a dialysis bag, dialysis was performed with distilled water for 72 h to remove impurities with a molecular weight of less than 10000, water being changed once every 12 hours, so as to obtain a nano-drug carrier covered with PEG2000 on the surface, and a pH value was adjusted to 7.4 to obtain a nano-drug carrier.

| (2) Formula: poly[2-carboxyacrylic acid] | 590 mg |
| polyethylene glycol-hydrazide | 2000 mg |

Preparation process: under the condition of magnetic stirring, with 1-(3-dimethylaminopropyl)-3-ethylcarbodiimide hydrochloride (1-ethyl-3-(3-dimethylaminopropyl)carbodiimide, EDC·HCl), and 1-hydroxybenzotriazole (N-hydroxybenzotriazole, HOBT) as a catalyst, 2 g of NH₂-PEG was added to a nano-drug carrier framework solution to modify a nano-drug carrier framework, a reaction was carried out overnight, the above solution was put into a dialysis bag, dialysis was performed with distilled water for 72 h to remove impurities with a molecular weight of less than 10000, water being changed once every 12 hours, so as to obtain a nano-drug carrier covered with PEG2000 on the surface, and a pH value was adjusted to 7.4 to obtain a nano-drug carrier.

| (3) Formula: hydrogenated lecithin | 60 mmol |
| cholesterol | 40 mmol |
| PEG2000-DSPE | 10 mmol |
| poly[2-carboxyacrylic acid] | 0.5% |

Preparation process: the above materials were dissolved in 50 mL of anhydrous ethanol, the anhydrous ethanol was removed by rotary evaporation to obtain a liposome membrane, 50 mL of water was added, hydration was performed, filtering was performed with a 200 nm microporous filter membrane, a pH value was adjusted to 7.4 with 0.001 N sodium hydroxide, poly[2-carboxyacrylic acid] outside the liposome that was not encapsulated by the liposome was removed by gel chromatography, and filtration was performed to obtain a nanoliposome that can actively load positively charged drugs, that is, a nano-drug carrier.

Efficacy of poly[2-carboxyacrylic acid] Nano-Drug Carrier

Figure 6:
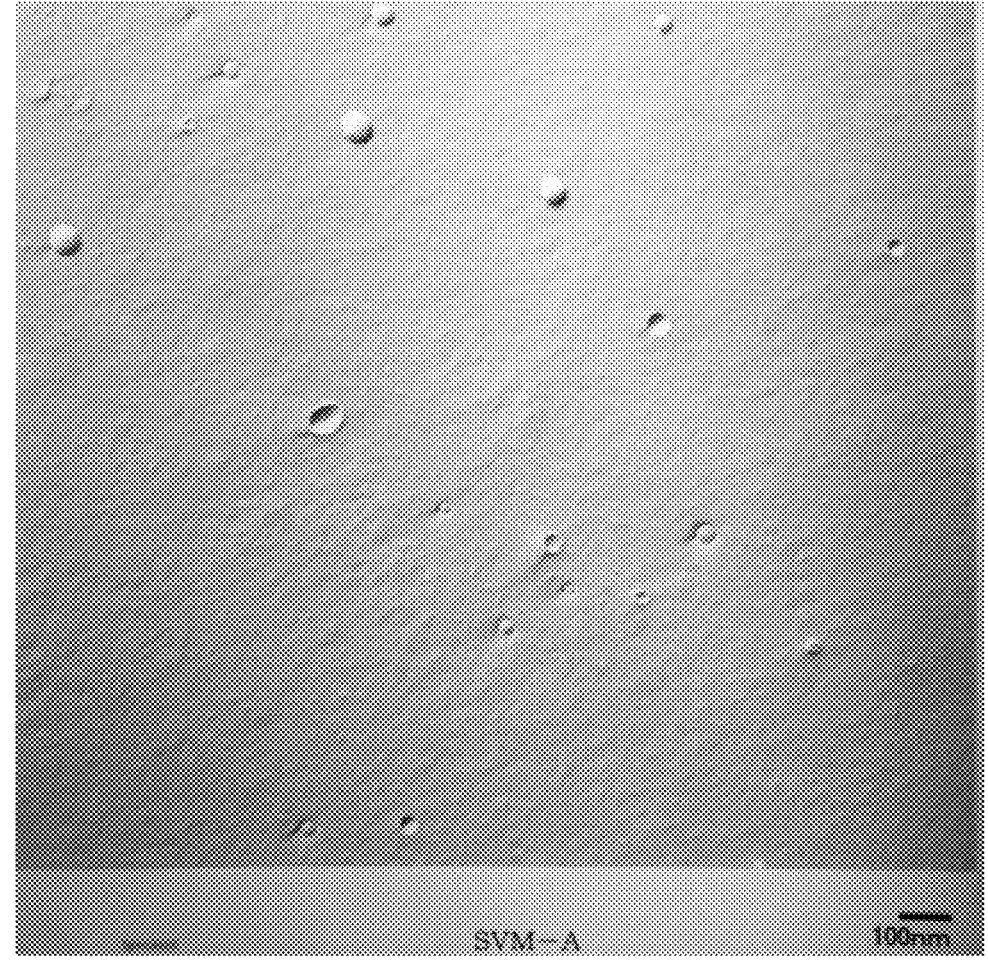
FIG. 6 shows an electron microscope photograph of poly[2-carboxyacrylic acid] nano-doxorubicin.
Figures 7, 8:
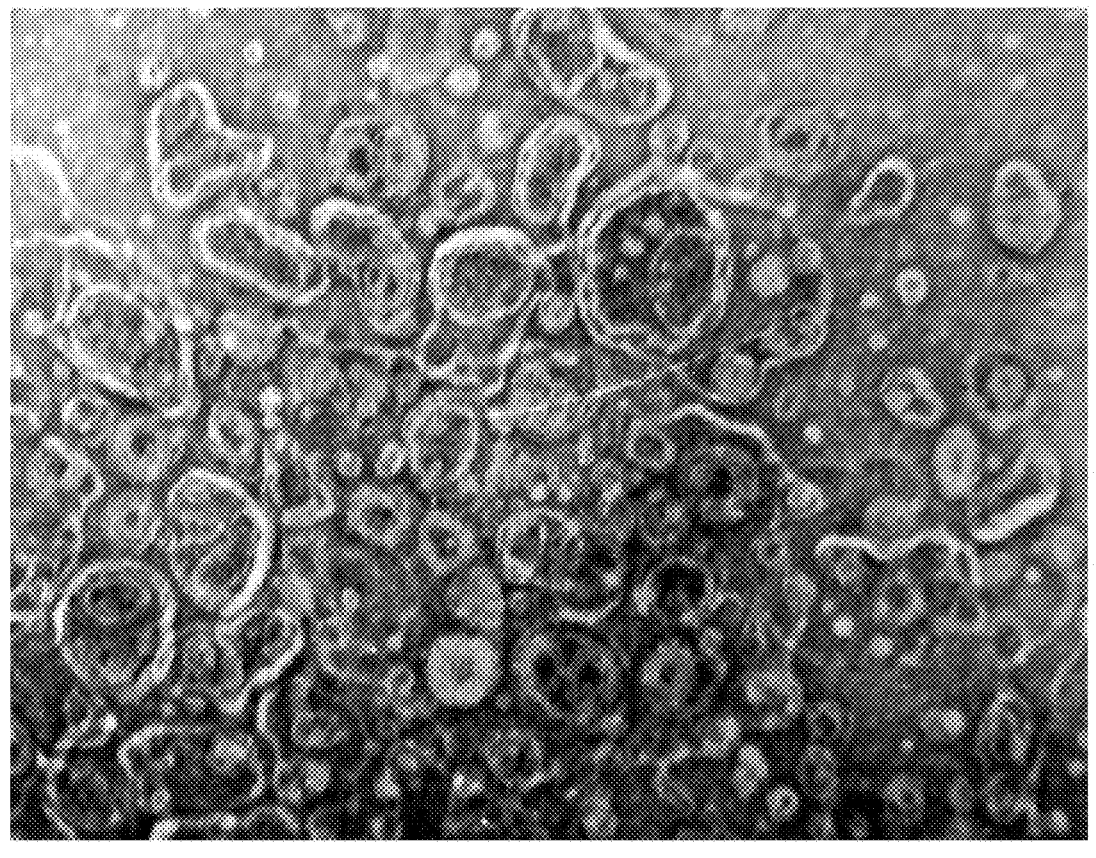
FIG. 7 shows an electron microscopy photograph of poly[2-carboxyacrylic acid] nano-doxorubicin liposome.
FIG. 8 is a structural schematic diagram of poly[2-carboxyacrylic acid].

Under a scanning electron microscope, the new nano-drug carrier has a spherical shape, uniform particle size and uniform distribution, and its Zeta potential can reach −52.5 mV By taking doxorubicin as an example, an animal model of sarcoma 180 in white mice and a C57BL6 tumor lung metastasis animal model proved that this nano-doxorubicin can significantly reduce the cardiotoxicity of doxorubicin, especially significantly reduce the incidence of heart failure caused by doxorubicin, and improve its anti-tumor effect (P<0.01). A rabbit liver cancer model was used to evaluate its efficacy. The results showed that its anti-cancer effect was significantly higher than that of doxorubicin (P<0.01). After the new nano-drug carrier was loaded with doxorubicin, nano-doxorubicin covered with polyethylene glycol on the surface is formed, after entering the body, the nano-doxorubicin covered with polyethylene glycol can circulate in the blood for a long time, and it is difficult for the nano-doxorubicin covered with polyethylene glycol to enter normal tissues with extremely low vascular permeability. However, the nano-doxorubicin covered with polyethylene glycol will passively accumulate into tumor tissues with high vascular permeability. Therefore, the anti-tumor effect of doxorubicin can be improved, and the toxic reaction of doxorubicin can be reduced. This product is added to freeze-dried doxorubicin to be shaken to form a nano-doxorubicin drug and can also transport other positively charged drugs. After entering the blood through intravenous drip, the new nano-drug carrier will accumulate in tumor tissues with high vascular permeability, infection sites or inflammation sites, thereby improving the efficacy of anti-cancer drugs, antibacterial drugs or anti-tumor drugs and reducing their adverse effects. The results of in vivo distribution study showed that the new nanoliposome drug carrier significantly reduced the distribution of doxorubicin to normal tissues and organs such as the heart, and significantly increased the distribution of tumors or infectious and inflammatory lesions. The results are shown in FIGS. 6-8.

The above-described examples are merely exemplary and illustrative of the invention and are not intended to limit the invention to the scope of the described examples. In addition, it should be understood by those skilled in the art that the present invention is not limited to the above-described examples, numerous variations and modifications may be made in light of the teachings of the present invention, and these variations and modifications all fall within the protection scope of the invention.

The invention claimed is:

1. A method comprising the steps of:

preparing an alkyl α-cyanoacrylate polymer;

forming a dispersion of the alkyl α-cyanoacrylate polymer in anhydrous ethanol;

adding an aqueous base to the dispersion to hydrolyze the alkyl α-cyanoacrylate polymer under alkaline conditions to obtain a hydrolysate solution, wherein:

all ester bonds of the alkyl α-cyanoacrylate polymer are hydrolyzed selectively under alkaline conditions and cyano groups are retained, and the hydrolysate solution includes poly[2-cyanoacrylic acid] dissolved in water, or all ester bonds and cyano groups of the alkyl α-cyanoacrylate polymer are hydrolyzed, and the hydrolysate solution includes poly[2-carboxyacrylic acid] dissolved in water; and for the hydrolysate solution that includes poly[2-cyanoacrylic acid]:

separating the poly[2-cyanoacrylic acid] from the hydrolysate solution and preparing a blank embolic microsphere using the poly[2-cyanoacrylic acid];

for the hydrolysate solution that includes poly[2-carboxyacrylic acid]:

separating the poly[2-carboxyacrylic acid] from the hydrolysate solution and preparing a nano-drug carrier using the poly[2-carboxyacrylic acid].

* * * * *